United States Patent [19]

Jelich et al.

[11] Patent Number: 4,874,424
[45] Date of Patent: Oct. 17, 1989

[54] HERBICIDAL AGENTS

[75] Inventors: Klaus Jelich, Wuppertal; Herbert Gayer, Monheim; Wolfgang Krämer, Burscheid; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 186,548

[22] Filed: Apr. 27, 1988

[30] Foreign Application Priority Data

May 8, 1987 [DE] Fed. Rep. of Germany ....... 3715248

[51] Int. Cl.$^4$ ............................................. A01N 37/34
[52] U.S. Cl. ........................................... 71/105; 71/98
[58] Field of Search ........................... 71/105, 118, 98

[56] References Cited

FOREIGN PATENT DOCUMENTS 0059536 9/1988 European Pat. Off. .

Primary Examiner—Catherine L. Mills
Attorney, Agent, or Firm—Sprung, Horn, Kramer & Woods

[57] ABSTRACT

A method of combating unwanted vegetation which comprises applying to such vegetation or to a locus from which it is desired to exclude such vegetation a herbicidally effective amount of an alkoximinoalkylamide of the formula

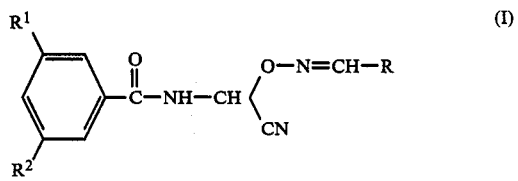

in which
R represents hydrogen or alkyl,
$R^1$ represents hydrogen, halogen, cyano, nitro, alkyl, alkoxy, alkylthio, halogenoalkyl, halogenoalkoxy, halogenoalkylthio, phenyl, phenoxy, formyl, alkoxycarbonyl, alkanoyl or alkoximinoalkyl and
$R^2$ represents halogen, cyano, nitro, alkyl, alkoxy, alkylthio, halogenoalkyl, halogenoalkoxy, halogenoalkylthio, phenyl phenoxy, formyl, alkoxycarbonyl, alkanoyl or alkoximinoalkyl.

5 Claims, No Drawings

HERBICIDAL AGENTS

The invention relates to the use of alkoximinoalkylamides as herbicides.

It is already known that certain substituted amides, such as, for example, 2-(4-chlorobenzoylamino)-2-ethoxy-acetonitrile, have herbicidal and fungicidal properties (compare, for example, European Pat. No. 59,536).

However, the herbicidal activity of these already known compounds against problem weeds is not completely satisfactory in all fields of use, especially at low application rates and concentrations.

It has been found that alkoximinoalkylamides of the general formula (I)

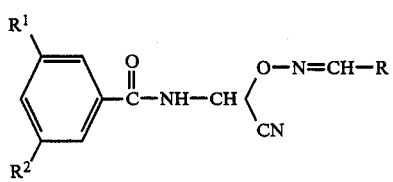

in which
R represents hydrogen or alkyl,
R¹ represents hydrogen, halogen, cyano, nitro, alkyl, alkoxy, alkylthio, halogenoalkyl, halogenoalkoxy, halogenoalkylthio, phenyl, phenoxy, formyl, alkoxycarbonyl, alkanoyl or alkoximinoalkyl and
R² represents halogen, cyano, nitro, alkyl, alkoxy, alkylthio, halogenoalkyl, halogenoalkoxy, halogenoalkylthio, phenyl, phenoxy, formyl, alkoxycarbonyl, alkanoyl or alkoximinoalkyl,
have herbicidal properties.

The compounds of the formula (I) can be in the form of geometric isomers or isomer mixtures of varying composition. Both the use of the pure isomers and that of the isomer mixtures are claimed according to the invention.

Surprisingly, the alkoximinoalkylamides of the general formula (I) which can be used according to the invention have considerably better herbicidal properties than the substituted amides known from the prior art, such as, for example, 2-(4-chlorobenzoylamino)-2-ethoxyacetonitrile, which are closely related compounds chemically and from the point of view of their action.

Formula (I) provides a general definition of the alkoximinoalkylamides which can be used according to the invention. Compounds of the formula (I) which can preferably be used are those in which
R represents hydrogen, or represents straight-chain or branched alkyl with 1 to 4 carbon atoms,
R¹ represents hydrogen, fluorine, chlorine, bromine, iodine, cyano or nitro, or represents in each case straight-chain or branched alkyl, alkoxy or alkylthio with in each case 1 to 4 carbon atoms, or represents in each case straight-chain or branched halogenoalkyl, halogenoalkoxy or halogenoalkylthio with in each case 1 to 4 carbon atoms and 1 to 9 identical or different halogen atoms, or represents phenyl, phenoxy or formyl, or represents alkanoyl with 1 to 5 carbon atoms, or represents alkoxycarbonyl with 1 to 5 carbon atoms, or represents alkoximinoalkyl with in each case 1 to 5 carbon atoms in the individual alkyl parts and
R² represents fluorine, chlorine, bromine, iodine, cyano or nitro, or represents in each case straight-chain or branched alkyl, alkoxy or alkylthio with in each case 1 to 4 carbon atoms, or represents in each case straight-chain or branched halogenoalkyl, halogenoalkoxy or halogenoalkylthio with in each case 1 to 4 carbon atoms and 1 to 9 identical or different halogen atoms, or represents phenyl, phenoxy or formyl, or represents alkanoyl with 1 to 5 carbon atoms, or represents alkoxycarbonyl with 1 to 5 carbon atoms, or represents alkoximinoalkyl with in each case 1 to 5 carbon atoms in the individual alkyl parts.

Compounds of the formula (I) which can particularly preferably be used are those in which
R represents hydrogen, methyl, ethyl, n- or i-propyl or t-butyl.
R¹ represents hydrogen, fluorine, chlorine, bromine, iodine, cyano, nitro, methyl, ethyl, n- or i-propyl, n-, i-, s- or t-butyl, methoxy, ethoxy, methylthio, trifluoromethyl, trifluoromethoxy, trifluoromethylthio, phenyl, phenoxy, formyl, acetyl, methoxycarbonyl, ethoxycarbonyl, methoximinomethyl, methoximinoethyl or ethoximinomethyl and
R² represents fluorine, chlorine, bromine, iodine, cyano, nitro, methyl, ethyl, n- or i-propyl, n-, i-, s- or t-butyl, methoxy, ethoxy, methylthio, trifluoromethyl, trifluoromethoxy, trifluoromethylthio, phenyl, phenoxy, formyl, acetyl, methoxycarbonyl, ethoxycarbonyl, methoximinomethyl, methoximinoethyl or ethoxyiminomethyl.

Compounds of the formula (I) which can especially preferably be used are those in which
R represents hydrogen, methyl, ethyl or t-butyl,
R¹ represents hydrogen, fluorine, chlorine, bromine, cyano, nitro, methyl, ethyl, methoxy, trifluoromethyl, phenyl, phenoxy, methoxycarbonyl, methoximinomethyl or methoximinoethyl and
R² represents fluorine, chlorine, bromine, cyano, nitro, methyl, ethyl, methoxy, trifluoromethyl, trifluoromethoxy, trifluoromethylthio, phenyl, phenoxy, methoxycarbonyl, methoximinomethyl or methoximinoethyl.

The following alkoximinoalkylamides of the general formula (I) may be mentioned specifically, in addition to the compounds mentioned in the preparation examples:

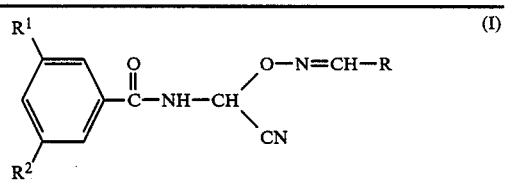

| R | R¹ | R² |
|---|----|----|
| H | Br | Br |
| H | Cl | Cl |
| CH₃ | Cl | Cl |
| H | F | F |
| CH₃ | Br | Br |
| H | H | Cl |
| CH₃ | H | Cl |
| CH₃ | F | F |
| CH₃ | CH₃ | CH₃ |
| H | H | CH₃ |

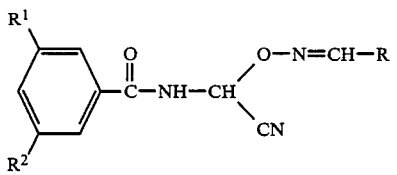  (I)

| R | R¹ | R² |
|---|----|----|
| H | CH₃ | CH₃ |
| H | H | CN |
| CH₃ | H | CN |
| CH₃ | H | NO₂ |
| H | H | NO₂ |
| CH₃ | NO₂ | NO₂ |
| H | CF₃ | CF₃ |
| CH₃ | CF₃ | CF₃ |
| H | H | SCF₃ |
| CH₃ | H | SCF₃ |
| H | H | OCF₃ |
| CH₃ | H | OCF₃ |

The alkoximinoalkylamides of the formula (I) which can be used according to the invention are the subject of Patent Application Ser. No. 081,952, filed Aug. 5, 1987, now pending, corresponding to German Patent Application P No. 3 627 072 of Aug. 9, 1986.

They are obtained by a process in which bromine-substituted amides of the formula (II)

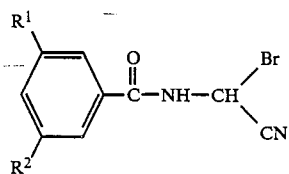  (II)

in which

R¹ and R² have the abovementioned meaning, are reacted with oximes of the formula (III)

HO—N=CH—R   (III)

in which

R has the abovementioned meaning, if appropriate in the presence of a diluent and if appropriate in the presence of an acid-binding agent.

If, for example, 2-(3-chlorobenzoylamino)-2-bromoacetonitrile and acetaldehyde oxime are used as starting substances, the course of the reaction in the preparation process can be represented by the following equation:

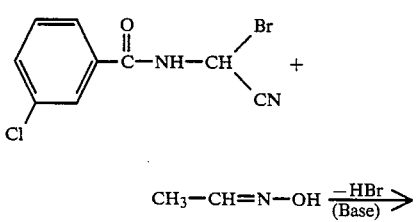

CH₃—CH=N—OH $\xrightarrow[\text{(Base)}]{-\text{HBr}}$

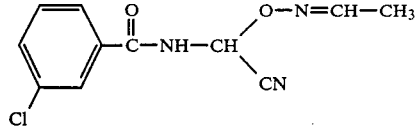

Formula (II) provides a general definition of the bromine-substituted amides required as starting substances for carrying out the preparation process. In this formula (II), R¹ and R² preferably represent those radicals which have already been mentioned as preferred for these substituents in connection with the description of the substances of the formula (I) which can be used according to the invention. The bromine-substituted amides of the formula (II) are known (compare, for example, European Pat. No. 59,536 or European Pat. No. 135,304).

Formula (III) provides a general definition of the oximes furthermore required as starting substances for carrying out the preparation process. In this formula (III), R preferably represents those radicals which have already been mentioned as preferred for this substituent in connection with the description of the substances of the formula (I) which can be used according to the invention.

The oximes of the formula (III) are generally known compounds of organic chemistry.

Possible diluents for carrying out the preparation process are inert organic solvents.

These include, in particular, aliphatic, alicyclic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

The preparation process is preferably carried out in the presence of a suitable acid-binding agent. These include, preferably, tertiary amines, such as triethylamine, N,N-dimethylaniline, pyridine, N,N-dimethylaminopyridine, diazabicyclooctane (DABCO), diazabicyclononene (DBN) or diazabicycloundecene (DBU), or alkali metal alcoholates, such as sodium methylate or sodium ethylate.

The reaction temperatures can be varied within a substantial range in carrying out the preparation process. The reaction is in general carried out at temperatures between −50° C. and +100° C., preferably at temperatures between −30° C. and +50° C.

For carrying out the preparation process, in general 1.0 to 3.0 mols, in particular 1.0 to 1.2 mols, of oxime of the formula (III) and 1.0 to 3.0 mols, in particular 1.0 to 2.0 mols, of acid-binding agent are employed per mol of bromine-substituted amide of the formula (II).

In a preferred procedure, the bromine-substituted amides of the formula (II) used as starting substances are prepared in a prior reaction directly in the reaction vessel by a process in which the corresponding cyanomethylamides of the formula (IV),

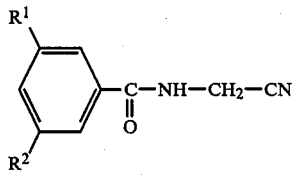

(IV)

in which
R¹ and R² have the abovementioned meaning, are brominated with a suitable brominating agent, such as, for example, with elemental bromine, in a suitable diluent, such as, for example, acetic acid or ethyl acetate, and if appropriate in the presence of a suitable acid catalyst, such as, for example, hydrobromic acid, at temperatures between −20° C. and +20° C., and the bromination products are then reacted directly in a "one-pot process".

The reaction is carried out and the reaction products of the formula (I) are worked up and isolated by methods analogous to known methods (compare European Pat. No. 59,536).

The active compounds which can be used according to the invention can be used as defoliants, desiccants, agents for destroying broad-leaved plants and, especially, as weed-killers. By weeds, in the broadest sense, there are to be understood all plants which grow in locations where they are undesired. Whether the substances which can be used according to the invention act as total or selective herbicides depends essentially on the amount used.

The active compounds which can be used according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds which can be used according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds which can be used according to the invention can be employed with particularly good success here for combating monocotyledon and dicotyledon weeds in monocotyledon and dicotyledon crops, such as, for example, wheat or soybean.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds which can be used according to the invention, as such or in the form of their formulations, can also be used, for combating weeds, in mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugarbeets and 4-amino-6-(1,1-dimethylethyl)-3-methylthio-1,2,4-triazin-5(4H)-one for combating weeds in soybeans.

Mixtures with chloroacetic acid N-(methoxymethyl)-2,6-diethylanilide; 2-chloro-4-ethylamino-6-isopropylamino-1,3,5-triazine; 5-amino-4-chloro-2-phenyl-2,3-dihydro-3-oxy-pyridazine; 2-chloro-N-{[(4-methoxy-6-methyl-1,3,5-triazin-2-yl)-amino]-carbonyl}-benzenesulphonamide; N,N-dimethyl-N'-(3-chloro-4-methylphenyl)-urea; exo-1-methyl-4-(1-methylethyl)-2-(2-methylphenyl-methoxy)-7-oxabicyclo(2,2,1)-heptane; ethyl 2-{[(4-chloro-6-methoxy-2-pyridinyl)-aminocarbonyl]-aminosulphonyl}-benzoate; 2-chloro-4-ethylamino-6-(3-cyanopropylamino)-1,3,5-triazine; 4-amino-6-t-butyl-3-ethylthio-1,2,4-triazin-5(4H)-one; S-ethyl N,N-di-n-propyl-thiocarbamate; N,N-dimethyl-N'(3-trifluoromethylphenyl)-urea; 1-methyl-3-phenyl-5-(3-trifluoromethylphenyl)-4-pyridone; trimethylsilylmethyl 2-[4-(3,5-dichloropyrid-2-yloxy)-phenoxy]-propionate; 2,4-dichlorophenoxyacetic acid; 2,4-dichlorophenoxypropionic acid; (4-chloro-2-methylphenoxy)-propionic acid; (2-methyl-4-chlorophenoxy)-acetic acid; methyl 2-[4,5-dihydro-4-methyl-4-(1-methylethyl)-5-oxo-1H-imidazol-2-yl]-4(5)-methylbenzoate; 2-[5-methyl-5-(1-methylethyl)-4-oxo-2-imidazolin-2-yl]-3-quinolinecarboxylic acid; 1-isobutylaminocarbonyl-2-imidazolidinone; N,N-dimethyl-N'-(4-isopropylphenyl)-urea; 3-cyclohexyl-5,6-trimethylene-uracil; 2-ethoxy-1-methyl-2-oxo-ethyl 5-[2-chloro-4-(trifluoromethyl)-phenoxy]-2-nitrobenzoate; N-methyl-2-(1,3-benzothiazol-2-yloxy)-acetanilide; 2-chloro-N-(2,6-dimethylphenyl)-N-[(1H)-pyrazol-1-yl-methyl]-acetamide; 2-ethyl-6-methyl-N-(1-methyl-2-methoxyethyl)-chloroacetanilide; 2-{[[((4-methoxy-6-methyl-1,3,5-triazin-2-yl)-amino)-carbonyl]-amino]-sulphonyl}-benzoic acid or the methyl ester thereof; N-(1-ethylpropyl)-3,4-dimethyl-2,6-dinitroaniline; α-chloro-2',6'-diethyl-N-(2-propoxyethyl)-acetanilide; 2-chloro-4,6-bis-(ethylamino)-1,3,5-triazine and methyl 2-{[(4,6-dimethyl-2-pyrimidinyl)-aminocarbonyl]-aminosulphonyl}-benzoate are also possible.

Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds which can be used according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds which can be used according to the invention can be seen from the following examples.

PREPARATION EXAMPLES

EXAMPLE 1

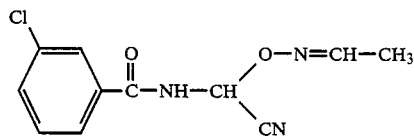

A few drops of bromine are added to 5.07 g (0.0261 mol) of 3-chlorobenzoylamino-acetonitrile in 250 ml of absolute ethyl acetate at 0° C. and the reaction is started by addition of a few drops of a 33% strength solution of hydrogen bromide in glacial acetic acid, the reaction mixture becoming decolorized. The remainder of the bromine [4.2 g (0.0262 mol) in total] is then slowly added, also at 0° C., the mixture is cooled to −25° C. when the addition has ended, and a mixture of 1.55 g (0.0262 mol) of acetaldehyde oxime and 5.3 g (0.0523 mol) of triethylamine in 50 ml of absolute ethyl acetate is then added in one portion, whereupon the reaction mixture warms to −10° C. and triethylamine hydrochloride precipitates out. The mixture is stirred at 0° C. for 15 minutes and filtered, the filtrate is concentrated and the oily residue is purified by chromatography on silica gel (mobile phase: methylene chloride).

1.3 g (20% of theory) of 2-(3-chlorobenzoylamino)-2-ethylideneiminoxy-acetonitrile are obtained as an E/Z mixture of melting point 92° C.

The following alkoximinoalkylamides of the general formula (I) are obtained in a corresponding manner and in accordance with the general statements on the preparation:

TABLE 1

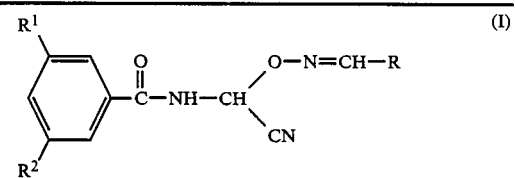

| Example no. | R | $R^1$ | $R^2$ | Physical properties |
|---|---|---|---|---|
| 2 | H | H | Br | m.p. 115° C. |
| 3 | CH$_3$ | H | Br | m.p. 96° C. |
| 4 | H | H | F | m.p. 127° C. |
| 5 | CH$_3$ | H | F | m.p. 152° C. |
| 6 | C$_2$H$_5$ | H | Br | m.p. 95° C. |

TABLE 1-continued

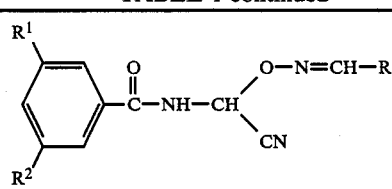

(I)

| Example no. | R | $R^1$ | $R^2$ | Physical properties |
|---|---|---|---|---|
| 7 | $C_2H_5$ | H | F | $^1$H—NMR*: 3.8 |
| 8 | $CH_3$ | H | $CH_3$ | $^1$H—NMR*: 1.95 |
| 9 | $C_2H_5$ | H | Cl | m.p. 83° C. |
| 10 | $C_2H_5$ | H | $CH_3$ | $^1$H—NMR*: 6.7 |
| 11 | $CH_3$ | Cl | Cl | m.p. 162–164° C. |
| 12 | H | H | Cl | m.p. 108–110° C. |
| 13 | H | H | CN | m.p. 146–148° C. |
| 14 | $CH_3$ | H | CN | m.p. 142–144° C. |
| 15 | $(CH_3)_3C—$ | H | CN | $^1$H—NMR*: 1.12 |
| 16 | H | H | $OCF_3$ | $^1$H—NMR*: 6.75 |
| 17 | $CH_3$ | H | $OCF_3$ | $^1$H—NMR*: 1.9 |
| 18 | $(CH_3)_3C—$ | H | $OCF_3$ | $^1$H—NMR*: 1.1 |
| 19 | H | Cl | Cl | m.p. 174–176° C. |
| 20 | $(CH_3)_3C—$ | Cl | Cl | $^1$H—NMR*: 1.12 |
| 21 | H | H | $NO_2$ | m.p. 142° C. |
| 22 | $CH_3$ | H | $NO_2$ | m.p. 93° C. |
| 23 | $(CH_3)_3C—$ | H | $NO_2$ | m.p. 114–116° C. |
| 24 | $CH_3$ | $CF_3$ | $CF_3$ | m.p. 96–98° C. |
| 25 | $CH_3$ | H | $SCF_3$ | m.p. 67° C. |
| 26 | H | H | $SCF_3$ | m.p. 106–108° C. |
| 27 | H | $CF_3$ | $CF_3$ | m.p. 142–144° C. |

*The $^1$H—NMR spectra were recorded in deuterochloroform ($CDCl_3$) with tetramethylsilane (TMS) as the internal standard. The chemical shift as the δ value in ppm is stated.

FORMULATION EXAMPLES (Data in percent by weight)

| 1. Wettable powder (Dispersible powder) | (a) | (b) | (c) | (d) | (e) | (f) |
|---|---|---|---|---|---|---|
| Active compound according to Preparation Example 4 | 10 | 20 | 35 | 50 | 65 | 85 |
| Dibutylnaphthalenesulphonate | 5 | 5 | 5 | 1 | 1 | 1 |
| Na lignin-sulphate | 5 | 5 | 5 | 5 | 5 | 5 |
| Highly disperse silicic acid | 5 | 5 | 5 | 5 | 5 | 5 |
| Ground natural minerals | 75 | 65 | 50 | 39 | 24 | 4 |

The active compound is mixed thoroughly with the additives and the mixture is ground to a powder. Before use, the wettable powder is stirred with water in an amount such that the dispersion thereby formed contains the active compound in the particular concentration desired.

| 2. Emulsion concentrate | (a) | (b) | (c) |
|---|---|---|---|
| Active compound according to Preparation Example 11 | 5 | 15 | 25 |
| Xylene | 75 | 65 | 55 |
| Cyclohexanone | 10 | 10 | 10 |
| Ca-dodecylbenzenesulphonate | 5 | 5 | 5 |
| Nonylphenol polyglycol ether | 5 | 5 | 5 |

The emulsion concentrate formed by mixing the active compound with the additives is diluted with water in an amount such that the mixture thereby formed contains the active compound in the particular concentration desired.

| 3. Granules | (a) | (b) | (c) | (d) | (e) |
|---|---|---|---|---|---|
| Active compound according to Preparation Example 11 | 1 | 3 | 7 | 15 | 20 |
| Ground natural minerals | 10 | 10 | 10 | 5 | 5 |
| Sand (particle size about 0.5–1.0 mm) | 88.3 | 86.2 | 82 | 78.5 | 73 |
| Polyvinyl acetate latex | 0.7 | 0.8 | 1 | 1.5 | 2 |

The active compound is finely ground with the ground minerals. The sand is taken in a mixer and latex and then the active compound mixture are added. The product is dried with hot air.

USE EXAMPLES

The compound shown below was employed as the comparison substance in the use example which follows:

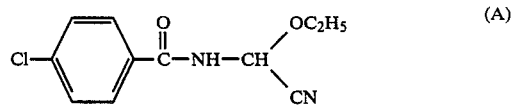
(A)

2-(4-chlorobenzoylamino)-2-ethoxy-acetonitrile (known from European Pat. No. 59,536)

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity compared with the comparison substance (A) is shown, for example, by the compounds according to the following preparation examples: 4 and 11.

TABLE A

| | | Pre-emergence test/Greenhouse. | | | | | | | |
|---|---|---|---|---|---|---|---|---|---|
| Active compound | Amount of active compound g/ha | Soybean | Wheat | Amaranthus | Polygonum | Portulak | Digitaria | Echinochloa | Panicum |
| (A) | (Known) 250 | 0 | 0 | 0 | 0 | 0 | 0 | 0 | 0 |

TABLE A-continued

| | | Pre-emergence test/Greenhouse. | | | | | | | |
|---|---|---|---|---|---|---|---|---|---|
| Active compound | Amount of active compound g/ha | Soybean | Wheat | Amaranthus | Polygonum | Portulak | Digitaria | Echinochloa | Panicum |
| 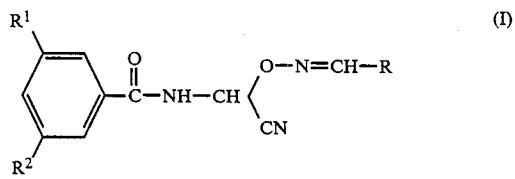 (A) | | | | | | | | | |
| (4) | 125 | 0 | 70 | 100 | 100 | 95 | 100 | 95 | 100 |
| 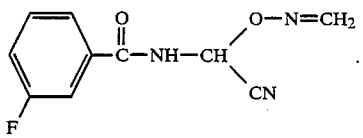 (4) | | | | | | | | | |
| (11) | 250 | 30 | 0 | 80 | 90 | 80 | 95 | 90 | 95 |
| 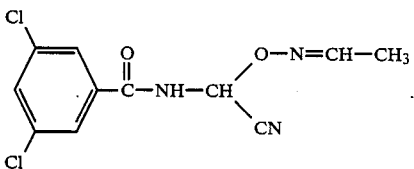 (11) | | | | | | | | | |

It will be appreciated that the instant specification and claims are set forth by way of illustration and not limitation, and that various modifications and changes may be made without departing from the spirit and scope of the present invention.

What is claimed is:

1. A method of combating unwanted vegetation which comprises applying to such vegetation or to a locus from which it is desired to exclude such vegetation a herbicidally effective amount of an alkoximinoalkylamide of the formula

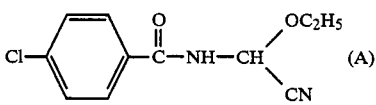 (I)

in which
R represents hydrogen, or represents straight-chain or branched alkyl with 1 to 4 carbon atoms,
$R^1$ represents hydrogen, fluorine, chlorine, bromine, iodine or nitro, or represents in each case straight-chain or branched halogenoalkyl with in each case 1 to 4 carbon atoms and 1 to 9 identical or different halogen atoms, and
$R^2$ represents fluorine, chlorine, bromine, iodine, cyano or nitro, or represents in each case straight-chain or branched alkyl with in each case 1 to 4 carbon atoms, or represents in each case straight-chain or branched halogenoalkyl, halogenoalkoxy or halogenoalkylthio with in each case 1 to 4 carbon atoms and 1 to 9 identical or different halogen atoms or represents alkoxycarbonyl with 1 to 5 carbon atoms.

2. A method according to claim 1, in which
R represents hydrogen, methyl, ethyl, n- or i-propyl or t-butyl,
$R^1$ represents hydrogen, fluorine, chlorine, bromine, iodine, nitro or trifluoromethyl and
$R^2$ represents fluorine, chlorine, bromine, iodine, cyano, nitro, methyl, ethyl, n- or i-propyl, n-, i-, s- or t-butyl, trifluoromethyl, trifluoromethoxy, trifluoromethylthio, methoxycarbonyl or ethoxycarbonyl.

3. A method according to claim 1, in which
R represents hydrogen, methyl, ethyl or t-butyl,
$R^1$ represents hydrogen, fluorine, chlorine, bromine, nitro or trifluoromethyl, and
$R^2$ represents fluorine, chlorine, bromine, cyano, nitro, methyl, ethyl, trifluoromethyl, trifluoromethoxy, trifluoromethylthio or methoxycarbonyl.

4. A method according to claim 1, in which said alkoximinoalkylamide is 2-(3-fluorobenzoylamino)-2-methylideneiminoxy-acetonitrile of the formula

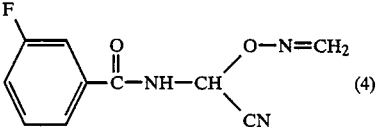

5. A method according to claim 1, in which said alkoximinoalkylamide is 2-(3,5-dichlorobenzoylamino)-2-ethylideneiminoxy-acetonitrile of the formula

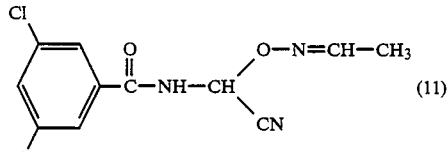

* * * * *